United States Patent [19]

Singh et al.

[11] Patent Number: 4,911,890

[45] Date of Patent: Mar. 27, 1990

[54] DEVICE FOR QUICKLY SENSING THE AMOUNT OF $O_2$ IN A COMBUSTION PRODUCT GAS

[75] Inventors: Jag J. Singh; William T. Davis, both of Yorktown; Richard L. Puster, Hampton, all of Va.

[73] Assignee: The United States of America as represented by the Administrator of the National Aeronautics and Space Administration, Washington, D.C.

[21] Appl. No.: 165,945

[22] Filed: Mar. 9, 1988

Related U.S. Application Data

[63] Continuation-in-part of Ser. No. 823,830, Jan. 29, 1986, abandoned, which is a continuation-in-part of Ser. No. 633,178, Jul. 23, 1984, abandoned.

[51] Int. Cl.[4] .............................................. G01N 27/30
[52] U.S. Cl. ........................................ 422/62; 422/98; 422/111; 422/126; 436/55; 436/137; 436/143; 431/12; 431/76
[58] Field of Search ...................... 422/62, 83, 58, 108, 422/111, 126; 436/55, 137, 143; 431/12, 76; 252/372

[56] References Cited

U.S. PATENT DOCUMENTS

| | | | |
|---|---|---|---|
| 4,187,486 | 2/1980 | Takahashi et al. | 436/137 X |
| 4,225,559 | 9/1980 | Achari et al. | 436/137 X |
| 4,298,573 | 11/1981 | Fujishiro | 436/137 X |
| 4,744,954 | 5/1988 | Campbell et al. | 422/98 |
| 4,770,758 | 9/1988 | Suzuki et al. | 422/98 X |

Primary Examiner—Barry S. Richman
Assistant Examiner—Lynn M. Kummert
Attorney, Agent, or Firm—George F. Helfrich; John R. Manning; Charles E. B. Glenn

[57] ABSTRACT

A sensing device 50 comprising an $O_2$ sensor 22, a pump 37, a compressor 19, and a heater 21 is provided to quickly sense the amount of $O_2$ in a combustion product gas. A sample of the combustion product gas is compressed to a pressure slightly above one atmosphere by compressor 19. Next, heater 21 heats the sample between 800° C. and 900° C. Next, pump 37 causes the sample to be flushed against electrode 32 located in $O_2$ sensor 22 6000 to 10,000 times per second. Reference air at approximately one atmosphere is provided to electrode 31 of $O_2$ sensor 22. Accordingly, $O_2$ sensor 22 produces a voltage which is proportional to the amount of oxygen in the combustion product gas. This voltage may be used to control the amount of $O_2$ entering into the combustion chamber 10 which produces the combustion product gas.

7 Claims, 2 Drawing Sheets

DEVICE FOR QUICKLY SENSING THE AMOUNT OF $O_2$ IN A COMBUSTION PRODUCT GAS

ORIGIN OF THE INVENTION

The invention described herein was made by an employee of the U.S. Government and may be manufactured and used by or for the Government for governmental purposes without the payment of any royalties thereon or therefor.

This application is a continuation-in-part of co-pending application Ser. No. 823,830, filed Jan. 29, 1986, which is a continuation-in-part of abandoned application, Ser. No. 633,178, filed 7/23/84.

TECHNICAL FIELD OF THE INVENTION

This invention relates to sensing the amount of a specific gas in a combustion product gas and more particularly to sensing the amount of oxygen in a combustion product gas.

BACKGROUND OF THE INVENTION quick sensing and subsequent controlling of the amount of oxygen ($O_2$) in a combustion product gas is necessary in various situations. For example, most engine test facilities in the U.S. use vitiated (oxygen enriched) combustion products expanded to either subsonic, supersonic, or hypersonic speeds to test and validate engine operation. To conduct nominal Mach 7 flow wind tunnel testing of air-breathing propulsion systems, the oxygen content of the combustion product flow gas must be equivalent to the oxygen content of the air. Too much oxygen may damage the engine; too little oxygen will result in reduced impulse. Also, this sensing of the amount of $O_2$ in the combustion product gas must be accomplished in a time interval smaller than the flow delivery system response and in a time frame that is a small fraction of the run time. Run times are often approximately 20 seconds.

Current $O_2$ sensing devices do not have response times which are quick enough to be utilized during such small time periods They are usually designed for use in boiler operations or steady state industrial processes where time is not of the essence. Currently available sensors have a response time of approximately five seconds. A sensor system response time of at least a quarter of a second is required in the above application. Such a sensor response time approximates real time since the response time of the valve controlling the amount of $O_2$ in the combustion chamber is about 0.25 second.

Accordingly, it is an object of this invention to quickly sense the amount of oxygen in a combustion product gas.

It is a further object of this invention to achieve the object in order to control the amount of oxygen in the combustion product to maximize efficiency and minimize pollution.

Other objects and advantages of this invention will become apparent hereinafter in the specification and drawings which follow.

SUMMARY OF THE INVENTION

According to the present invention, the foregoing and additional objects are obtained by providing a device for quickly sensing the amount of oxygen in a combustion product gas. A test sample from a combustion product gas is pressurized, heated, and introduced into a product gas cavity of an $O_2$ sensor. A heated ceramic electrolyte disc coated with platinum electrodes serves as a shared wall between this product gas cavity and a reference air cavity. This disc generates a voltage output which is proportional to the partial pressure difference of the $O_2$ in both the product gas and the reference air which are introduced at one atmosphere and normal to opposite sides of the disc. A vacuum pump keeps the product gas moving quickly through the product gas cavity, thus allowing a quick sensing of the $O_2$ content of the product gas If necessary, additional $O_2$ may be introduced into the combustion chamber or an alarm sounded if an excess of $O_2$ is present. The quick sensing of the present invention allows essentially real time control of the additional $O_2$, which is an essential feature for a vitiated product gas used for engine testing.

DETAILED DESCRIPTION OF THE INVENTION

Figure 1:
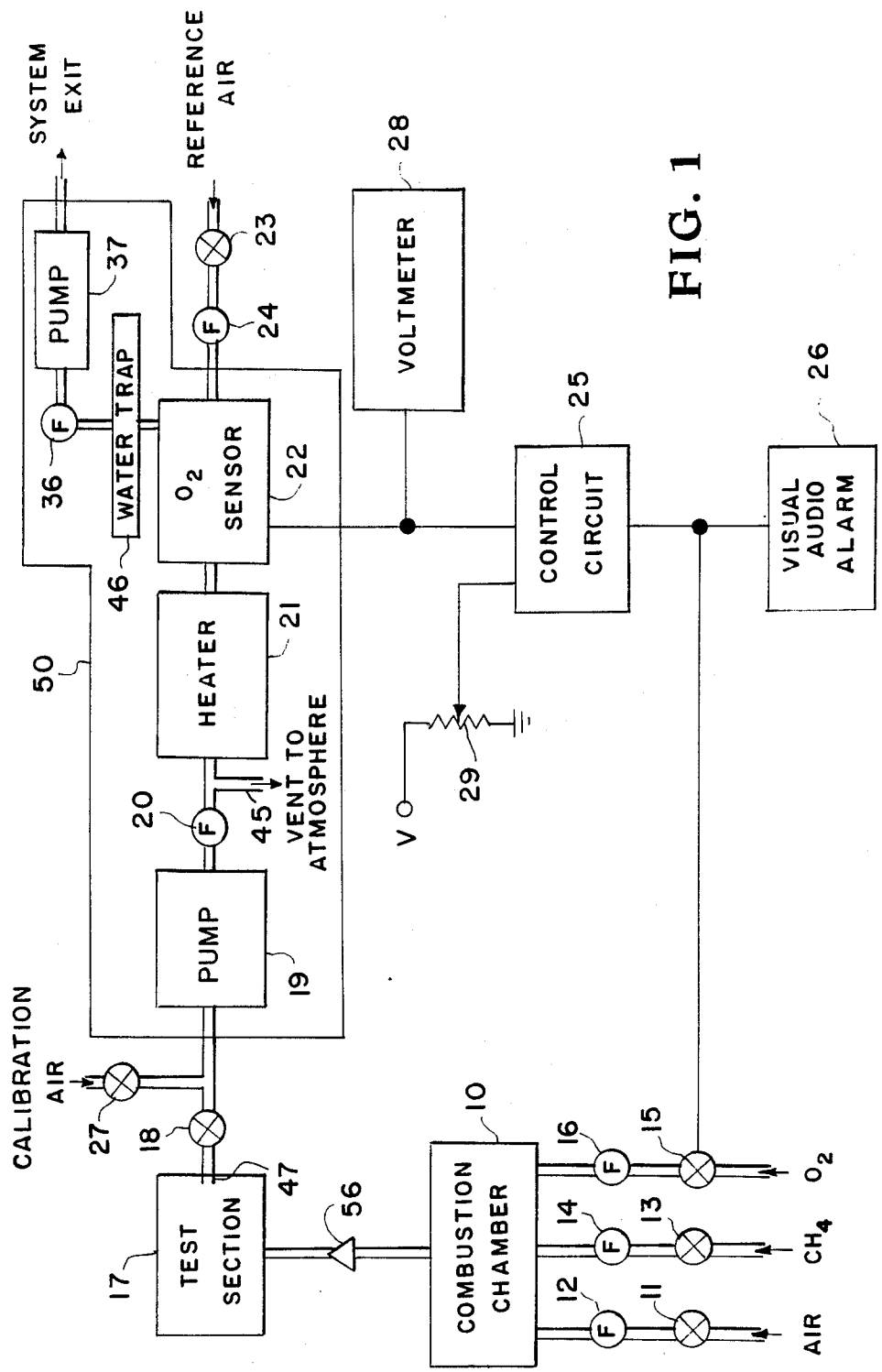
FIG. 1 is a schematic diagram of a combustion system employing the sensing device of the present invention.

As illustrated in FIG. 1, a combustion system employing a sensing device 50 is shown. Air udder pressure flows through a controlled delivery valve 11 and a flow meter 12 into combustion chamber 10; a gas under pressure flows through a controlled delivery valve 13 and a flow meter 14 into combustion chamber 10; and oxygen under pressure flows through a controlled delivery valve 15 and a flow meter 16 into combustion chamber 10. The gas flowing through valve 13 may be any hydrocarbon gas such as $CH_4$, $C_2H_6$, ... $C_xH_y$, or any mixture of the preceding. The mixture of gases flowing into combustion chamber 10 is burned and the product gas of the combustion flow is expanded by nozzle 56 into a test section 17. The flow may be subsonic, supersonic, or hypersonic. A sample of the product gas in test section 17 flows through a probe 47, a valve 18, a compression pump 19, a flow meter 20 and a heater 21 into $O_2$ sensor 22. The flow of the sampled combustion product is always subsonic with a normal pitot type probe 47 and viscous. Accordingly, the diameter of the tubing through which the gas flows must be large enough or the length short enough to avoid volumetric choking (a limit to volumetric flow rate for a given length and diameter of tubing). Probe 47 must have a blunt entrance normal to the sample flow to always maintain the sample at subsonic flow rates. High enthalpy flows will require a cooled or ceramic probe 47. Cooling may be accomplished by water cooling probe 47.

Figure 2:
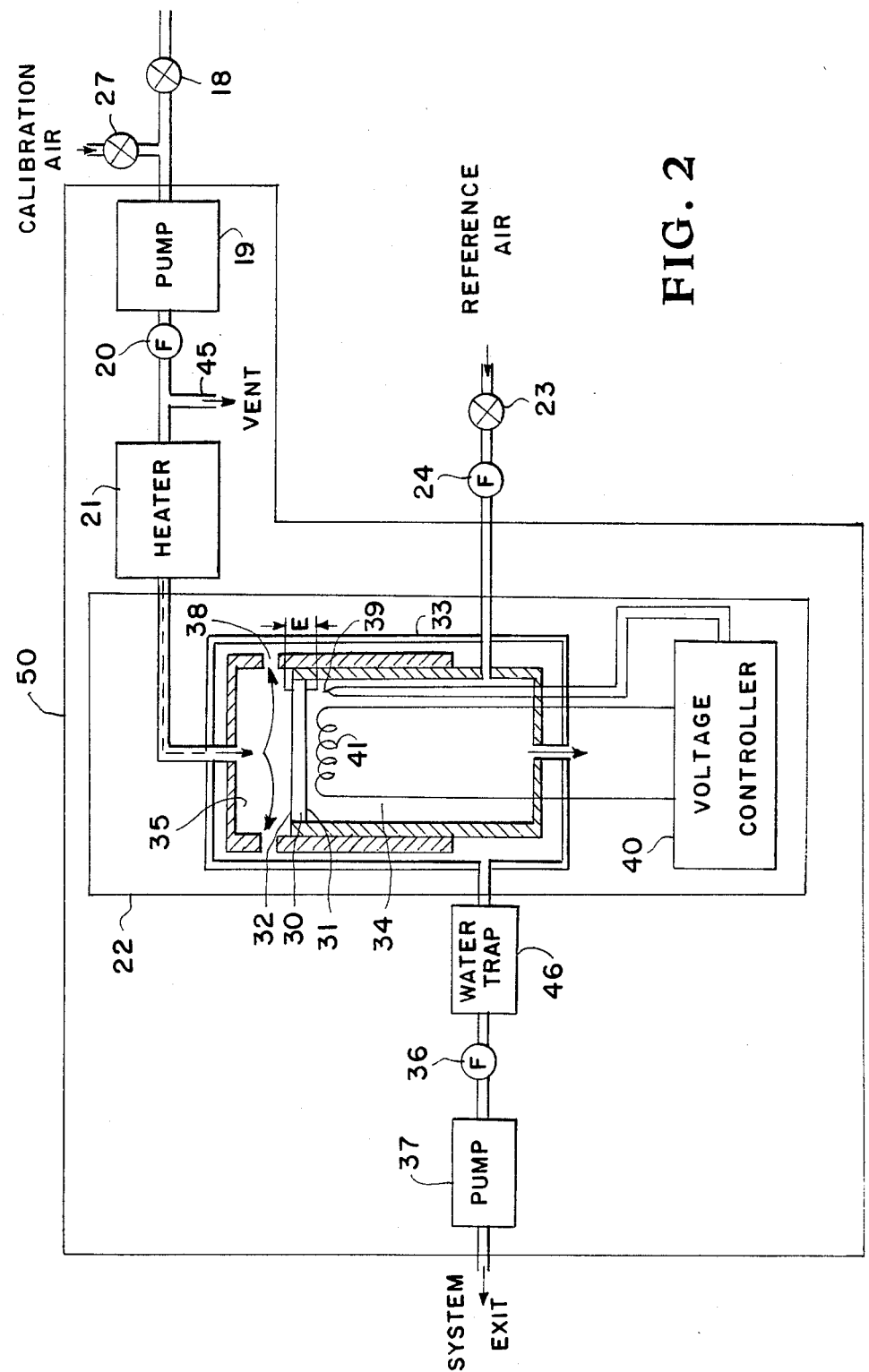
FIG. 2 is an exposed view of the sensing device of the present invention.

Referring now to FIG. 2, sensing device 50 comprising an $O_2$ sensor 22, a pump 37, a compression pump 19, a heater 21, and reference air is shown. When a sample of the product test gas flows through valve 18, it is compressed to a pressure slightly above one atmosphere and has flow energy added by compression pump 19. To ensure that the sample enters $O_2$ sensor 22 at a pressure of approximately one atmosphere, an atmospheric vent 45 which leads to the atmosphere is employed. An alternate arrangement would be to use a precision pressure regulator in lieu of atmospheric vent 45 and a compression pump 19 with a higher compression ratio.

Next, the sample is heated by heater 21 to a temperature of 300° C. to 800° C.

Next, the sample enters product gas cavity 35 of $O_2$ sensor 22. The $O_2$ sensor 22 consists of a high temperature, $Y_2O_3$ stabilized $ZrO_2$ ceramic electrolyte disc 30 coated with porous platinum electrodes 31 and 32. The platinum electrodes 31 and 32 are porous enough to permit ready diffusion of $O_2$. The disc 30 and electrodes 31 and 32 are enclosed in a cylindrical enclosure 33 with disc 30 dividing enclosure 33 into product gas cavity 35 and reference air cavity 34. Reference air is introduced into reference air cavity 34 through valve 23 at a pressure of nearly one atmosphere and comes into contact with electrode 31. The sample comes into contact with electrode 32.

The $O_2$ sensor 22 produces a voltage output E across electrodes 31 and 32 which is given by the following equation:

$$E = AT \ln \frac{P_1}{P_2} + C(P) \quad (1)$$

where A is a mathematical constant, T is the temperature of disc 30, $P_1$ is the partial pressure of oxygen on electrode 31, $P_2$ is the partial pressure of oxygen on electrode 32 and C(P) is the cell constant determined by calibration with known gas mixtures at known pressures. Usually operation at 1 atmosphere ($\pm 2$ percent) is desired since increasing cell pressure increases the $ZrO_2$ sensor output. It is apparent from equation (1) that when the partial pressures of the gas from test section 17 and reference air are compared at the same total pressure, the voltage output E will not be directly proportional to the difference of the two partial pressures. The reason is that the cell constant C(P) is not equal to zero. Hence, C(P) must be determined. This calibration should be done daily since atmospheric pollution changes the calibration slightly each day. To do this valve 18 is closed and clean calibration air at one atmosphere pressure is applied through a valve 27, flow meter 20, and heater 21 to $O_2$ sensor 22. Consequently, the partial pressure of calibration air is compared to the partial pressure of reference air and if the flow rates of flow meters 20 and 24 are the same the output E of $O_2$ sensor 22 will be C(P). Referring once again to FIG. 1, this output is measured by a voltmeter 28. Then the slider of potentiometer 29, with a voltage V applied to it, is adjusted to apply C(P) to control circuit 25. Control circuit 25 subtracts the output of potentiometer 29 from the output of $O_2$ sensor 22. Next, mathematical constant A is determined by introducing a reference gas of known pressure, temperature, and mixture through valve 27, flow meter 20, and heater 21 to $O_2$ sensor 22. Once output voltage E is obtained, equation (1) may be easily solved for A.

Referring once again to FIG. 2, the voltage E produced across electrodes 31 and 32 is extremely sensitive to disc 30 temperature. Hence, it is important that the temperature of disc 30 be maintained at a high level between 800° C. and 900° C. An optimal temperature is 843° C. To maintain such a temperature, a NiCr/NiAl thermocouple 39 monitors the temperature of disc 30. The output of thermocouple 39 is compared with a set voltage in a voltage controller 40 to produce an error signal which is used by voltage controller 40 to produce a voltage across a heating coil 41 to maintain the temperature of disc 30. In order to avoid an increase in sensor response time caused by the cooling effect of the lower temperature gas from test section 17, the sample is heated by heater 21 before it reaches the $O_2$ sensor 22 to at least 300° C. and no more than 800° C.

The sample should be flushed normal against electrode 32 from 8400 to 10,000 times per second to ensure response time which is less than 0.2 second for the entire combustion system. The $O_2$ sensor 22 has a response time of 30 milliseconds. Therefore, it is apparent that the elements shown are important to achieve the system response since the $O_2$ sensor 22 is relatively fast but delivery and control of the sampled gas must be done as shown. The test gas is from 800° C. to 3000° C. The sensor could not survive direct impingement of high temperature, ultra-fast combustion products The probe collects the gas and cools it to an acceptable level before compression pump 19 is encountered. The required flushing is accomplished by a vacuum pump 37 and compression pump 19. Product gas cavity 35 has a circumferential slot opening 38. In one embodiment of the present invention, product gas cavity 35 has a volume of slightly less than one cubic centimeter and circumferential slot opening 38 ha a width of 0.5 mm and is located approximately 0.5 mm from electrode 32. The sample gas is compressed by compressor 19 to a pressure of nearly one atmosphere before entering product gas cavity 35. Next, the sample is pumped out of product gas cavity 35 and through circumferential slot 38, cylindrical enclosure 33, flow meter 36, water trap 46, and a system exit at a rate of 6000 cubic centimeters per second to 10,000 ccm/sec by pump 37. Accordingly, the response of the control sensing device 50 is less than 0.20 seconds.

Such a quick response time allows for a control of the amount of $O_2$ in combustion chamber 10. Referring now to FIG. 1, $O_2$ sensor 22 produces a voltage E continuously ad enables the combustion system to respond to sample change in 0.2 seconds. This system response is usually much faster than most control valves resulting in a real time update to the $O_2$ valve controller. It is possible to have faster response with short lengths of tubing and very compact systems. This voltage E passes through control circuit 25, which subtracts the output of potentiometer 29 and controls the controller (15a) for valve 15. Large valves usually have a response time of 0.25 second or slower. Accordingly, the 0.20 second response time of the sensing device 50 results in sensing device 50 operating in essentially real time relative to the control valve 15. If the control valve 15 is relatively large, then one-fifth second is adequate If the system is small, building the components as compact and as small as possible is necessary. If the amount of sensed $O_2$ exceeds a predetermined amount, visual and audio alarm 26 may be excited and the amount of $O_2$ flowing into combustion chamber 10 is decreased by control valve 15. Likewise, i the amount of sensed $O_2$ is less than a predetermined amount, the amount of 02 flowing into combustion chamber 10 is increased by control valve 15. Thus, the amount of $O_2$ in the combustion product gas is quickly sensed and controlled to the desired valve. For example, it is essential when testing engines that the flight conditions be duplicated and that the gas have twenty-one percent molar concentration of $O_2$.

An important feature of this invention is its ability to be used at a wide range of Mach numbers from 0 to 8 with gas temperatures from 800° C. to 3000° C. The test gas is regulated to simulate various flight altitudes as well. The unique arrangement shown will always adjust the sample gas to a sea level reference. The present invention may be used at altitudes ranging from 0 to above 130,000 feet as simulated by a propulsion type wind tunnel.

What is claimed is:

1. A device for quickly sensing the amount of oxygen in a combustion product gas produced in a combustion chamber comprising:
    a means for obtaining a sample of the combustion product gas;
    a means for compressing the sample to a pressure slightly greater than one atmosphere;
    a means for heating the sample within a temperature range from 300° C. to 800° C;
    a cylindrical enclosure;
    a product gas cavity inside said cylindrical enclosure;
    a reference air cavity inside said cylindrical enclosure;
    a means for providing reference air to said reference air cavity at a pressure of approximately one atmosphere;
    a ceramic electrolyte disc which is coated on both sides with platinum electrodes with sufficient porosity to permit diffusion of the oxygen present in the reference air and test sample gas, is positioned as a shared wall between said product gas cavity and said reference air cavity, and produces a voltage output;
    a means for heating said disc from 800° C.;
    a means for flushing said compressed and heated sample through said product gas cavity and impinging said sample against said platinum electrode in the product gas cavity approximately 8400 to 10,000 times per second;
    a means for sensing the voltage output of said disc which is proportional to the amount of oxygen in the sample and therefore the combustion product gas according to the following equation:
$$E = AT\ln(P_1/P_2) + C(P)$$
where E is the voltage output produced by the platinum electrolyte disc, T is the temperature of said ceramic electrolyte discs, $P_1$ is the partial pressure of the oxygen in the reference air against one side of said disc, $P_2$ is the partial pressure of the oxygen in the sample gas against the other side of said disc, A is a mathematical constant, and C(P) is the disc constant.

2. The device of claim 1 including a combustion chamber for producing the combustion product gas sample and regulating the amount of oxygen into the combustion chamber which produces the sample in response to said voltage output.

3. The device of claim 1 wherein said means for flushing comprises a vacuum pump which pumps the sample through said product gas cavity, through a water trap, and through an exit.

4. The device of claim 3 wherein said vacuum pump provides a flow rate of the products gas ranging from approximately 6000 to 10,000 cubic centimeters per second and said product gas cavity has a volume of approximately one cubic centimeter.

5. The device of claim 1 wherein the combustion product gas produced flows at a supersonic rate and said means for obtaining a sample is a probe with a blunt end which is normal to the flow to ensure a subsonic flow to said means for compressing.

6. The device of claim 5 wherein said probe includes water-cooling means.

7. The device of claim 5 wherein said probe is composed of a ceramic material.

* * * * *